United States Patent [19]
Nelson

[11] Patent Number: 4,821,737
[45] Date of Patent: Apr. 18, 1989

[54] WATER SEPARATOR

[75] Inventor: Peter E. Nelson, Englewood, Colo.

[73] Assignee: The BOC Group, Inc., Montvale, N.J.

[21] Appl. No.: 900,030

[22] Filed: Aug. 25, 1986

[51] Int. Cl.$^4$ ............................................. A61B 5/08
[52] U.S. Cl. .................................. 128/730; 128/719;
    55/189; 55/204; 73/863.21
[58] Field of Search ............... 128/716, 718, 719-720,
    128/730, 205.12, 205.27, 205.29; 55/189, 204;
    73/863.21

[56]       References Cited
    U.S. PATENT DOCUMENTS

| | | | |
|---|---|---|---|
| 4,197,858 | 4/1980 | Osborn | 128/719 X |
| 4,292,978 | 10/1981 | Guth | 128/719 X |
| 4,304,578 | 12/1981 | Hakala et al. | 128/719 X |
| 4,446,869 | 5/1984 | Knodle | 128/716 |
| 4,546,778 | 10/1985 | Sullivan | 128/719 X |
| 4,558,708 | 12/1985 | Labuda et al. | 128/719 |
| 4,579,568 | 4/1986 | Ricciardelli et al. | 128/719 X |

Primary Examiner—Kyle L. Howell
Assistant Examiner—Angela D. Sykes
Attorney, Agent, or Firm—Larry R. Cassett; Roger M. Rathbun

[57] ABSTRACT

A water separator is disclosed for removing water from a minute flow of gas/water sampled from a patients exhalation and prior to the gas being introduced into an analyzer. The separator comprises a housing with an inlet, an outlet, and a pair of chambers in series through which the sample is drawn. The first chamber has a pair of substantially closely aligned wall surfaces of predetermined narrow distance from each other such that the surface tension causes the liquid in the sample to adhere to the wall surfaces. As the sample progresses to the second chamber, the wall surfaces are further apart and thus the tension effect is broken and only the gas continues through the second chamber to the separator outlet. A drain is located in the lower part of the first chamber for withdrawal of the accumulated liquid from that chamber.

9 Claims, 1 Drawing Sheet

WATER SEPARATOR

BACKGROUND OF THE INVENTION

Water separators are conventionally utilized in connection with monitors for analyzing one or more of the constituents of a patient's exhaled breath. Typically, such separators are used with carbon dioxidate analyzers that withdraw a sample of the patients exhalation and which detect and display the carbon dioxide component by use of an infrared analyzer. Such IR analyzers are readily available commercially, however it is paramount that the moisture in the breath sample be removed prior to that sample entering the IR analyzer. Various types of such water separators have been proposed for such applications, including those disclosed in U.S. Pat. No. 4,600,412 to Liston et al.; U.S. Pat. No. 4,446,869 to Knodle and U.S. Pat. No. 4,382,806 of Hakala et al. Each has certain advantageous features and are typical of the type of water separator used with a breath monitor where the flow of gas is minute, but the need to remove liquid is critical.

SUMMARY OF THE INVENTION

In accordance with this invention, a water separator is provided that readily and efficiently separates water from a stream of gas/liquid withdrawn from a patient's exhaled breath prior to entering an instrument for anlayzing one or more constitutents of that breath gas.

The water separator may be easily manufactured in two basic components making up a housing and fitted with inlet, outlet and water drain fittings. Actual water separation takes place by means of surface tension where the gas containing the water is passed through a first chamber constructed by a pair of substantially flat, planar parallel surfaces that are spaced apart a narrow predetermined distance. As the gas liquid passes through the first chamber, the narrow passageway causes the liquid to adhere to the flat planar surfaces and the gas continues through relatively unimpeded. Thus the gas passes into a second chamber that has its side surfaces spaced further apart than the surfaces of the first chamber causing a break in the surface tension phenomenon and the gas continues on via an outlet to the gas analyzer. A drain in the lower most portion of the first chamber is provided to remove accumulated liquid that flows downward to the bottom of the first chamber by gravity or slight vacuum. By use of slight vacuum, the water separator can function in a variety of positions independent of gravity. Thus, the water separator is relatively easy to manufacture, being constructed of very few parts and yet which effectively removes the water from the gas/water stream withdrawn from the patient circuit for analysis.

The foregoing and other advantages and features of the present invention will become readily apparent from the following description.

BRIEF DESCRIPTION OF THE DRAWINGS

The invention is diagrammatically illustrated by way of examples in the drawings appended hereto, in which.

DESCRIPTION OF THE PREFERRED EMBODIMENT

Figure 1:
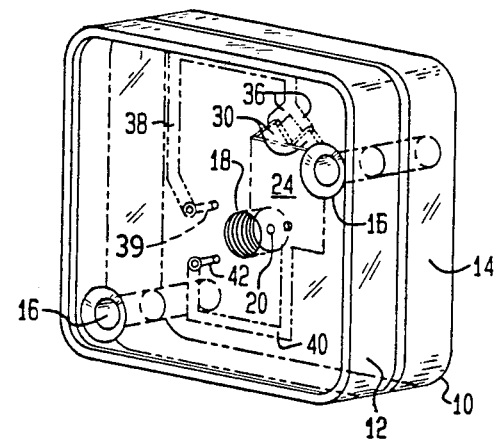
FIG. 1 is an isometric view of the water separator of the present invention showing the chambers and passageways therethrough.

Referring now to FIG. 1 there is shown an isometric view of a water separator 10 and which comprises a housing made up of two sections, identified for purposes of identification as a front section 12 and a rear section 14. The front and rear sections 12 and 14 are joined together to construct water separator 10 and that joining can, of course, be by a variety of methods. In the performed embodiment, holes 16 are drilled through both the front and rear sections 12 and 14 for suitable bolts and nuts, not shown, to firmly secure the sections together. The housing itself is preferably of a transparent plastic material such as a polycarbonate so that a visible inspection can be made of the interior passageways when desired.

An inlet 18 is formed in the front section 12 and may be threaded to secure a fitting. The inlet 18 receives the sample of withdrawn gas from the patient's breath and which may contain water. Flow of this withdrawn stream is generally a very low flow and typically is in the range of 25 to 500 ml./min.

Figure 2:
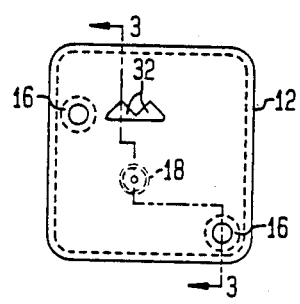
FIG. 2 is a front view of one of the two main stream of the housing of the water separator.
Figure 3:
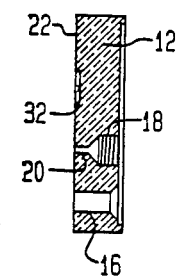
FIG. 3 is a cross-section view of the section of FIG. 2 taken along the lines 3—3 of FIG. 2.

Turning briefly to FIGS. 2 and 3, the inlet 18 can be seen in more detail and narrows down to a bore 20 of approximately 0.040 inches in diameter at its innermost point. The inner surface 22 of the front section 12 is a flat, planar surface, the purpose of which will be later described.

The bore 20 of inlet 18 opens into a first chamber 24 at or near the lower portion of first chamber 24. The first chamber 24 is thus a narrow passageway formed between the front and rear section 12 and 14 when they are affixed together.

Figure 4:
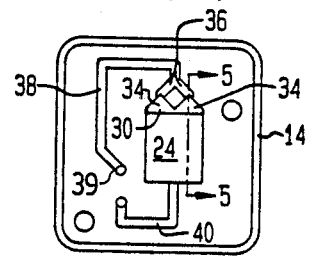
FIG. 4 is a front view of the second of the two main sections of the housing of the water separator.
Figure 5:
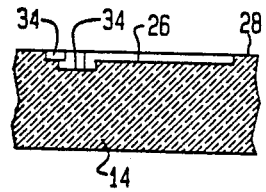
FIG. 5 is a broken, cross-sectional view of a portion of the section of FIG. 5 taken along the lines 5—5 of FIG. 4.

Turning briefly to FIGS. 4 and 5, the first chamber 24 is formed by the recess 26 on the inner surface 28 of the rear section 14 and is typically about 0.030 inches deep. When front section 12 is then joined together with the rear section 14 as in FIG. 1, the flat planar surface 22 of front section 12 is parallel to the recess 26 in the inner surface 28 of rear section 14, thus creating an extremely narrow passageway of predetermined area and having a cross-sectional depth of about 0.030 inches.

Returning to FIG. 1, it can be seen that the moisture laden sample that is drawn in through inlet 18 to the first chamber 24 continues upwardly through the first chamber 24 and is thus drawn between two flat planar surfaces that have an extremely narrow gap or distance there between. Thus, the surface tension effect causes water to cling to the sides of the first chamber 24 and the gas continues to pass through the first chamber 24.

At the top of the first chamber 24, there is a second chamber 30 that is provided to break the surface tension of first chamber 24. That break in surface tension is accomplished through the side walls of the second chambers being spaced sufficiently further apart than the side walls of the first chamber.

Again referring to FIGS. 2-5, the second chamber 30 may be of various configurations, however, in the preferred embodiment, the second chamber 30 comprises a pair of triangular shaped passages and are formed by a pair of triangular shaped recesses 32, joined together at their bottoms, on the inner surface 22 of the front section 12. The depth of the recesses 32 may be about 0.030 inches. The use of dual passages is preferred in that if one of the passages is occluded by the water, its resistance increases and thus the other passage will selectively increase its flow.

Corresponding mating recesses 34 are formed in the inner surface 28 of rear section 14 and the depth of such recesses 34 are about 0.060 into inner surface 28 or about 0.030 inches deeper than the recess 26 formed in the first chamber 24 (see FIG. 5).

At the top apex of each of the triangular-shaped passages of the second chamber 30 are passageways 36 that join together into passageway 38 formed in the inner surface 28 of the rear section 14 and which communicates with outlet 39 drilled through the rear section 14 from passageway 38 out through the outer surface. Again, a suitable fitting such as a male stub (not shown) may be fitted to the outlet 39 for connection to flexible tubing to withdraw the gas from outlet 39 of the water separator 10.

A further passageway 40, formed in the inner surface 28 of rear section 14 communicates with the bottom of first chamber 24 for the withdrawal of accumulated water as it moves downwardly along the walls of the first chamber 24 by gravity or slight vacuum. Passageway 40 ends at water outlet 42 which, again, is a bore drilled through the rear section 14 so that water may be continuously withdrawn from water outlet 42 by a slight vacuum.

I claim:

1. A water separator for use with a breath gas analyzer, for analyzing the breath of a patient, said separator comprising; a housing having an inlet for receiving gas/liquid removed as a sample from the patient's breath and an outlet for discharging gas from said water separator to the analyzer, first and second chambers formed in said housing means intermediate said inlet and said outlet, said first chamber adapted to receive said gas/liquid from said inlet and having a pair of substantially closely aligned wall surfaces of predetermined narrow distance from each other, said aligned surfaces sufficiently close to remove liquid from said gas/liquid stream passing from said inlet to said outlet by surface tension with said liquid adapted to adhere to said aligned surfaces, said second chamber adapted to receive said gas stream from said first chamber, said second chamber having wall surfaces spaced apart a wider distance than said wall surfaces of said first chamber to break the surface tension effect, said outlet communicating with said second chamber for removal of the gas, a liquid reservoir formed ins aid first chamber and a liquid drain outlet communicating with said first chamber at a point remote from said second chamber and oppositely disposed from said second chamber with respect to said inlet, said liquid drain outlet communicating liquid from said first chamber to said liquid reservoir.

2. A water separator as defined in claim 1 wherein said second chamber comprises at least two passages joined at their bottoms and each having independent discharge passageways.

3. A water separator as defined in claim 2 wherein said at least two passages comprise triangular passages having said discharge passageways at their top apexes.

4. A water separator as defined in claim 1 wherein said closely aligned wall surfaces of said first chamber are approximately 0.030 inches apart.

5. A water separator as defined in claim 1 wherein said closely aligned wall surfaces comprise two parallel, planar surfaces.

6. A water separator as defined in claim 5 wherein said parallel planar surfaces are approximately 0.030 inches apart.

7. A water separator as defined in claim 6 wherein said wall surfaces of said second chamber are approximately 0.060 inches apart.

8. A water separator for use with a breath gas analyzer for analyzing a constituent of a patient's breath, said separator comprising; a housing having an inlet for receiving gas/liquid removed as a sample from the patient's breath, and an outlet for discharging gas from said water separator to the constituent analyzer, first and second chambers formed in said housing intermediate said inlet and said outlet and having a pair of parallel planar wall surfaces of predetermined narrow distance from each other, said parallel surfaces sufficiently close to remove liquid from said gas/liquid stream passing from said inlet to said outlet by surface tension with said liquid adapted to adhere to said aligned surfaces, said second chamber receiving said gas stream from said first chamber, said second chamber having a pair of parallel wall surfaces spaced apart a further distance and parallel to said wall surfaces of said first chamber to break the surface tension effect, said outlet communicating with said second chamber for removal of the gas, a liquid reservoir formed ins aid first chamber and a liquid drail outlet communicating with said first chamber at a point remote from said second chamber and oppositely disposed from said second chamber with respect to said inlet, said liquid drain outlet communicating liquid from said first chamber to said liquid reservoir.

9. A method of removing moisture from a sample of a patients exhalation comprising the steps of:
 a. removing a sample of the patients exhaled breath;
 b. separating moisture from the sample by introducing the sample to an inlet of a first chamber and then through said first chamber having closely spaced wall surfaces of predetermined narrow distance apart to ahere the moisture by surface tension to the wall surfaces;
 c. passing the dry sample from the first chamber into a second chamber having spaced wall surfaces of a further distance apart to break the surface tension effect;
 d. draining the moisture from said first chamber at a point further remote from said second chamber than the inlet to said first chamber; and
 e. drawing the sample from the second chamber.

* * * * *